United States Patent [19]

Cheslak

[11] Patent Number: 4,765,701
[45] Date of Patent: Aug. 23, 1988

[54] ILLUMINATOR OPTICAL FIBER ROD

[75] Inventor: Leonard W. Cheslak, Tustin, Calif.

[73] Assignee: Poly-Optical Products, Inc., Santa Ana, Calif.

[21] Appl. No.: 9,413

[22] Filed: Jan. 30, 1987

[51] Int. Cl.⁴ .............................. G02B 6/00; F21V 7/04
[52] U.S. Cl. .............................. 350/96.10; 350/96.19; 350/96.29; 362/26; 362/32
[58] Field of Search .............. 350/96.10, 96.15, 96.16, 350/96.20, 96.29, 96.30, 96.19; 362/32, 23, 26; 250/227

[56] References Cited

U.S. PATENT DOCUMENTS

| | | | |
|---|---|---|---|
| 2,909,857 | 10/1959 | Wilson | 362/32 X |
| 3,692,383 | 9/1972 | Herod et al. | 350/96.10 |
| 3,829,675 | 8/1974 | Mariani | 350/96.10 X |
| 4,052,120 | 10/1977 | Sick et al. | 350/96.10 X |
| 4,128,332 | 12/1978 | Rowe | 350/96.10 |
| 4,141,058 | 2/1979 | Mizohata et al. | 362/32 |
| 4,172,631 | 10/1979 | Yevick | 350/96.10 |
| 4,173,390 | 11/1979 | Kach | 350/96.16 |
| 4,196,962 | 4/1980 | Sick | 350/96.10 |
| 4,561,043 | 12/1985 | Thompson | 362/32 |
| 4,585,298 | 4/1986 | Mori | 350/96.10 |
| 4,678,279 | 7/1987 | Mori | 350/96.10 X |
| 4,717,226 | 1/1988 | Mori | 350/96.10 |
| 4,726,641 | 2/1988 | Mori | 350/96.10 |
| 4,730,883 | 3/1988 | Mori | 350/96.10 |
| 4,732,442 | 3/1988 | Mori | 350/96.10 |
| 4,733,332 | 3/1988 | Yamashita | 362/32 |

FOREIGN PATENT DOCUMENTS 56-32104 4/1981 Japan ............................. 350/96.10

Primary Examiner—William L. Sikes
Assistant Examiner—Brian M. Healy
Attorney, Agent, or Firm—Nilsson, Robbins, Dalgarn, Berliner, Carson & Wurst

[57] ABSTRACT

An illuminator formed from an optically transmissive body which is characterized by internal reflection and which has formed at discrete locations along its length one or more recesses. Each of these recesses includes two opposing surfaces which depend angularly inward from the body to define an included angle therebetween. This illuminator may be used in conjunction with a panel formed with discrete locations of transparency which are positioned contiguous to one or more of the recesses to insure that light passing out from the illuminator will be directed through the transparent location of the panel.

36 Claims, 1 Drawing Sheet

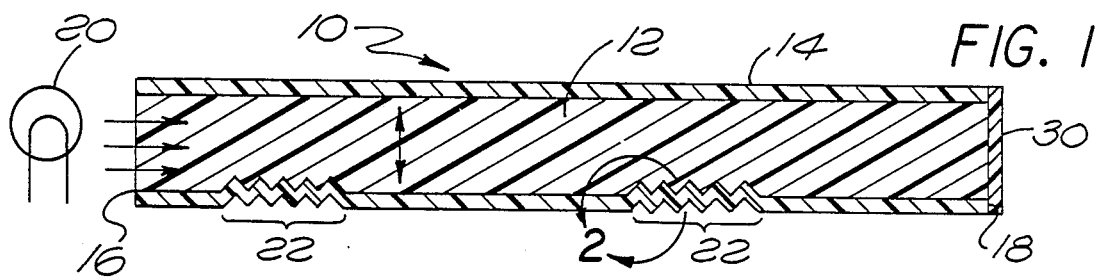
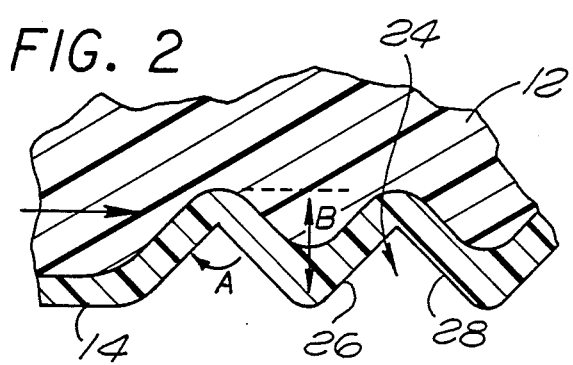
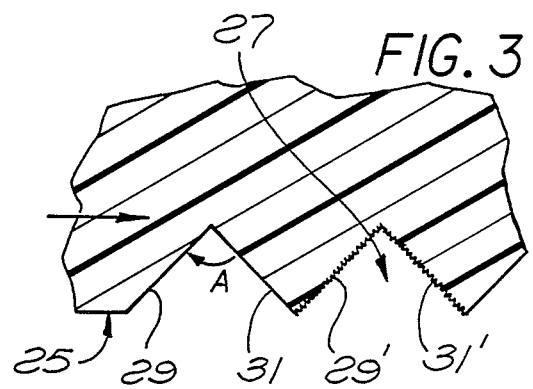
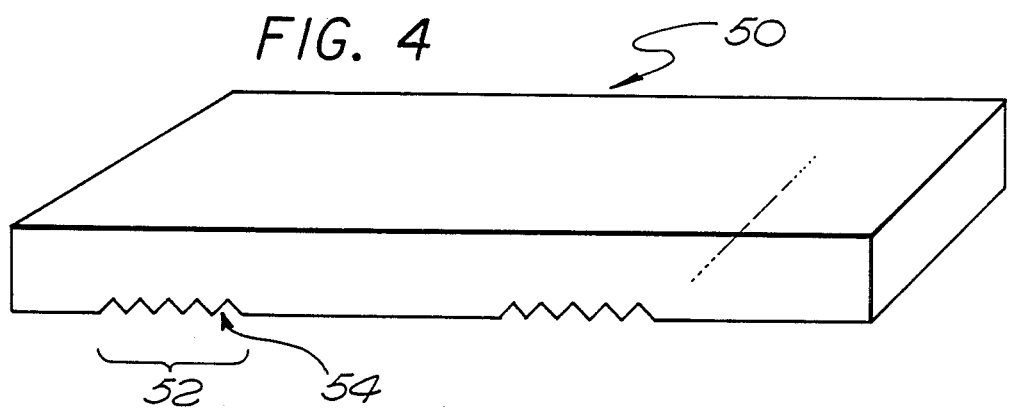
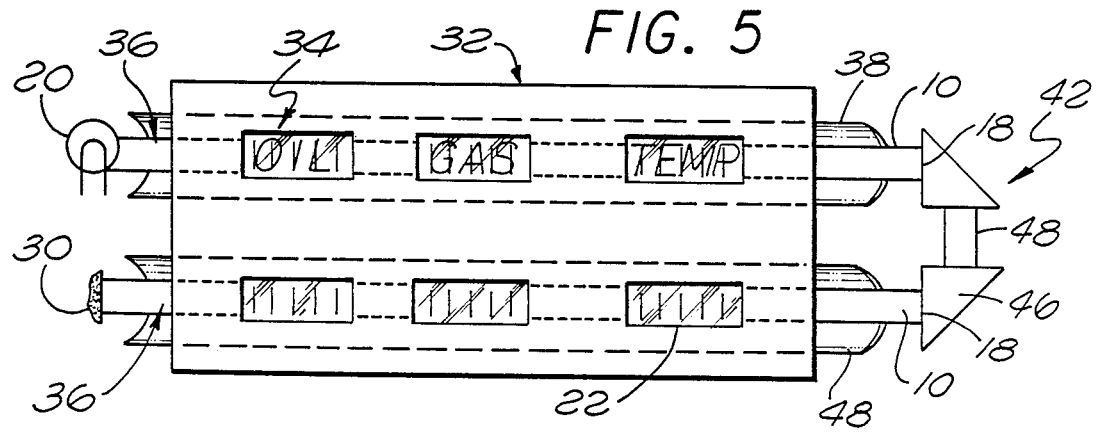

ILLUMINATOR OPTICAL FIBER ROD

BACKGROUND OF THE INVENTION

The present invention is directed to the art of fiber optics, specifically to the use of optically transmissive bodies as illuminating devices.

Fiber optics, including both filament and other shaped bodies have found use in many applications, for instance, as ornamental lighting, display lighting and in the transmission of information.

One particular application for which fiber optics have been used is as illuminators. An illuminator is a device where the light, which is normally traversing longitudinally through the optically transmissive body, is diverted laterally outward from the body at various points to illuminate given areas.

Illuminators are formed by modifying a optically transmissive body to "leak" an incremental amount of the total amount of light passing therethrough laterally outward. Thus by using only a single light source, i.e., a bulb, numercus areas may be lighted using one or more illuminators prepared in this manner. Since the illumination of these multiple areas would normally require more than bulb, the efficiency of the overall lighting system in greatly increased by the use of an optical illuminator.

There are numerous methods by which an fiber optic can be prepared to effect a lateral transmission of light. For example, the fiber optic body can be cut with grooves at various points along its length, with one or more of the groove surfaces coated with a reflective material. This reflective material will reflect any light which impinges upon it. By properly positioning the grooved surfaces light can be directed in any desired direction.

An angular mirror arrangement imbedded in or laid along the fiber optic body can be substituted for the mirror coated groove surfaces. Fiber optic bodies modified in this manner will transmit light in a similar manner as the light impinges upon the mirrored surfaces.

Examples of optical illuminators prepared by the discussed techniques are generally disclosed in U.S. Pat. Nos. 4,052,120 issued to Sick et al.; 4,173,390 issued to Kach; and 4,196,962 issued to Sick.

Another example of an optical illuminator is where a fiber optic is coated along a portion of its peripheral surface with an illuminant material. This illuminant surface functions as a secondary light source reflecting light generally inward and toward the opposite side of the body, if such side is not coated out therethrough. A fiber optic illuminator prepared by this technique is disclosed in U.S. Pat. No. 4,128,332 issued to Rowe.

Another technique of modifying a fiber optic body to prepare an illuminating device involves roughing a portion of the peripheral surface of the fiber optic body. The light will pass out through this roughened surface. A fiber optic prepared in this manner is disclosed in U.S. Pat. No. 3,829,675.

Fiber optics have also be prepared, as disclosed in U.S. Pat. No. 4,172,631 issued to Yevick, to possess spaced apart longitudinal reflecting surfaces. The fibers are compatibly grooved and laid on a reflective material. The finished product thus includes a multiplicity of mirrored surfaces positioned along the length of the fibers. The height or depth of these surfaces are specifically calculated to provide for the reflection radially inward of an incrementally increasing quantity of the total light passing through the fiber. This light will pass across and through the opposite side of the fiber.

While optical illuminators prepared by the discussed techniques provide some lateral light emission, the degree of light emitted is not always adequate, and the methods of preparing these optical illuminating devices is generally costly. That is, the imbedding of mirror assemblies into a fiber optic or the coating of grooved surfaces is costly. There thus exists a need for a technique by which optical illuminators can be easily prepared in an economical manner. There also exists a need for an optical illuminator which provides greater illumination.

SUMMARY OF THE INVENTION

The present invention achieves the above objectives by providing a illuminator formed from an optically transmissive body having at defined locations at least a first recess, which recess is defined by two opposing surfaces which angle inwardly toward each other. Light which impinges upon these surfaces is deflected toward and will pass out through the opposing side of the body, provided such side is not coated by a nontransparent material.

By the appropriate placement of each recess light can be emitted laterally outward upon any intended object or location. Furthermore, by forming the optically illuminator to possess a series of such recesses, a larger degree of light can be emitted.

The illuminator of the invention is advantageously utilized in combination with a panel which is transparent at one or more desired locations. By properly forming the recesses and/or a series of recesses in the optical illuminator, light can be emitted through the transparent locations of the panel.

DESCRIPTION OF THE DRAWINGS

The present invention may be better understood, and its numerous objectives will become apparent, from the following Figures, wherein like reference numerals refer to like elements in the several Figures and wherein:

FIG. 1 is a lengthwise cross-sectional view of a fiber optic illuminator in accordance an embodiment of the invention;

FIG. 2 is an enlarged portion of FIG. 1 at line 2;

FIG. 3 is an enlarged cross-sectional view of a series of recesses formed in a fiber optic illuminator in accordance with another embodiment of the invention;

FIG. 4 is a perspective view of an illuminator in accordance with another embodiment of the invention, formed from a generally rectangular optically transmissive body; and FIG. 5 is a front view of a display panel incorporating fiber optic illuminators of the invention.

DESCRIPTION OF THE INVENTION

The present invention is directed at an illuminator formed from an optically transmissive body, which body has the characteristic of total internal reflection and is formed with one or more recesses. Each of these recesses is defined by two opposing surfaces which angle inwardly toward each other. A portion of the light traveling through the body is deflected by these surfaces in a direction to be emitted through the opposing side of the body.

Referring to FIG. 1, a longitudinal cross-sectional view of an illuminator in accordance with an embodiment of the invention is seen generally at 10.

It should be noted that while the illuminator 10 illustrated in FIG. 1 is formed from a optically transmissive fiber, that is, a fiber characterized by total internal reflection, the optically transmissive body from which the illuminator of the invention may be formed includes any desired shape, e.g., filamentous or rectangular. The only requirement is that the material from which the body is prepared is the type of material which will provide that light can be directed through the length of the body by substantially total internal reflection.

Generally, the types of materials from which optically transmissive bodies useful for the purposes of the invention can be prepared are well known in the art. These materials will be those which allow for the transmission of light but have a refractive index greater than the refractive index of air. More expensive materials include various types of glass, while other materials include various types of acrylics and polystyrenes. Typically, non-filamentous bodies will be constructed from a single material characterized by a refractive index which allows for the internal reflection to occur at the boundary of that material and the surrounding air. Fibrous optically transmissive bodies may be prepared in this manner but may also be formed to have a core prepared from a material having a first refractive index, which core is enveloped by another material having a second refractive index. By providing that the material forming the core is of a greater refractive index, the desired internal reflection of light is obtained.

As seen in FIG. 1, the fibrous illuminator 10 is formed with an internal core 12 of material which is substantially transparent and has a first refractive index. This transparent core 12 is substantially sheathed by an outer cladding 14 of a substantially transparent material having a second refractive index. The internal reflection is provided by insuring that the refractive index of the cladding 14 material is less than the refractive index of the core 12 material.

The optical fiber illuminator 10 has first and second ends 16 and 18, with end 16 being illuminated by a light source 20. The light source 20, which may be an incandescent bulb, may be used to illuminate the end 16 of more than one illuminator 10. This would increase the efficiency of the use of the particular light source 20.

The light will pass through the end 16 and travel through the core 12 in accordance with known principles of internal reflection, i.e., Snell's law. In accordance with Snell's law, a substantial portion of the light traveling through the core 12 will be angularly deflected across the core 12 at the interface between the core 12 and the outer cladding 14. It is further believed that if the light is directed at this interface at other than within a prescribed range of angles, the light will pass through the outer clouding 14. It is this general principle of which the invention makes use; however, since this is only a theory, the present invention should not be bound or limited in any manner by it.

The illuminator 10 of the invention is formed with one or more recesses 24, with the recesses 24 of the illustrated embodiment being arranged as a series of recesses 24 contained in a defined region, with one such region generally indicated at 22. The recesses 24 which form the region 22 are defined by two opposing surfaces 26 and 28 which angle inwardly toward the fiber optic to define an included angle therebetween which, as will be discussed further herein, is such to cause the deflection of light toward the opposing side of the illuminator 10. This deflection occurs at the interface between the core 12 and the cladding 14; however, it is to be understood that an illuminator prepared from a fiber optic comprised of a single material will allow for this deflection at the interface between the material and the surrounding air.

Thus, each of the recess 24 of the regions 22 function to cause an emission of light out from the opposing side of the illuminator 10. By utilizing more than one recess 24 to form a recess region 22, a larger amount of light is directed out of the illuminator. Depending on the amount of light which is desired to be emitted in this manner, a single recess may be formed in the fiber optic, or numerous recesses 24 may be formed at spaced apart locations.

The individual recesses 24 of the defined region 22 are preferably formed in a manner to insure that when the fiber optic being used to construct the illuminator 10 includes an outer cladding 14 that this outer cladding 14 remains intact. That is, the manner by which the individual recesses 24 are formed should insure the integrity of the cladding 14. Methods useful for manufacturing the optical illuminator 10 of the invention in this manner include, but are not limited to, the various cast molding processes or injection molding process, whereby an optical fiber is continuously molded with one or more of the defined regions 22 of recesses 24 being formed during the molding process, or by a hot or cold embossing method where the individual recesses 24 are formed by deforming the surface of a virgin fiber optical rod at desired locations.

When preparing the individual recesses 24 by one of these methods or any equivalent method, the material of the fiber optic will flow somewhat after the recess 24 is formed. The result is that the recesses 24, which are generally rectangular, are shaped to have their various corners rounded off, as seen better in FIG. 2. As will be described in greater detail below, other methods may be used to form the individual recesses 24, e.g., machine cutting the optic fiber, with the resulting recess 24 having a more pronounced rectangular shape, as better seen in FIG. 3.

While the individual recesses 24 may be spatially separated in the surface of the illuminator 10, even when arranged within a defined region 22 in accordance with a preferred embodiment, the individual recesses 24 are arranged contiguous to each other, as best seen in FIGS. 1 and 2. This manner of contiguously positioning the individual recesses 24 maximizes the illumination which will pass out of the opposing side of the illuminator 10.

Referring specifically to FIG. 2, an individual recess 24 in accordance with an embodiment of the invention will be described in greater detail. These recesses 24 are defined by two opposing surfaces 26 and 28 which angle inwardly to define an "included" angle A therebetween, which angle A is generally from about seventy degrees to about one hundred ten degrees, more preferably from about eighty-five to about ninety-five degrees. By forming the surfaces 26 and 28 at this angle A, light which impinges on either one of these surface 26 or 28 will be deflected toward and through the opposing side of the illuminator 10, provided that such side is not coated with an opaque material. If an opaque covered fiber optic is used, such coating must be removed in order to allow for the emission of the light.

The depth of the individual recesses 24 is not critical to the invention, that is, the individual recesses 24 do not have to be deep in comparison to the diameter of the optical fiber comprising illuminator 10 in order to function in accordance with the invention. Generally the depth, indicated by the Arrow B, of the individual recesses 24 may vary from about two to about eighty percent of the cross-sectional distance of the fiber optic, as indicated by the Arrow C in FIG. 1, or for that matter the cross-sectional distance of any shaped body forming an illuminator in accordance with the invention. As stated, this distance is not critical, since it has been found that the amount of light deflected will not significantly differ with varying recess depths. However, the depth of the recess 24 will effect the amount of light which will continue to pass through the illuminator 10, with the amount of light diminishing as the depth of the recess 24 increases. Thus, it is preferable to provide the recesses 24 with depths of from about two to about twenty-six percent of the cross-sectional distance, more preferably from about two to about sixteen percent.

By way of example, recesses of varying "included angles" and varying "depths" were formed in optical fibers having diameters of three sixteenths (3/16) of an inch. These fibers were of the type having an acrylic inner core and a styrene outer cladding. Light from a three candle power incandescent bulb was directed through the prepared fiber optic illuminators. The amount of light which was emitted out through the various recesses was measured, with good illumination, between one hundred and two hundred foot lamberts being demonstrated for recesses of varying depths, that is, recesses having depths of from 0.005" to 0.15", which is substantially equivalent to a depth of from about two to about eighty percent of the cross-sectional distance of the fiber. However, good illumination, again between one hundred and two hundred foot lamberts, was found only with those recesses having an included angle of from seventy to one hundred ten degrees, with even better illumination, that is, closer to two hundred foot lamberts, found for recesses having an included angle of from eighty-five to ninety-five degrees.

Referring now to FIG. 3, a differently configured recess 27 in accordance with another embodiment of the invention will be described. This recess 27, which is formed in an illuminator 25, is also defined by two opposing surfaces 29 and 31 which angle inwardly toward each other. However, the recess 27 of this embodiment is formed by machine cutting and as a result possesses sharper edges and corners than the recess 24 previously described. This type of recess 27, when formed in a virgin fiber optic having an outer cladding, will not retain the cladding as illustrated for the recess 24. Further, while both recesses 24 and 27 provide ample illumination for the purposes of the invention, by forming the recess with a more rounded internal apex, that is, the top of the recess inside the illuminator as seen in FIG. 2, the illumination obtained is greater. The reason for this effect is believed to result from more light being deflected from the rounded sloped surface of the recess 24, as compared to the generally straight surface of the recess 27; however, this is merely a theory and is not to be construed to limit the scope of the invention.

In order to increase the illuminating characteristic of the recesses described herein, it is preferable to texturize one or both of the recesses surfaces, with surfaces 29' and 31' of the recess 27' being illustrated as texturized in FIG. 3. This texturization increases the quantity of light which passes through the respective surface. The surfaces can be texturized by any suitable process, e.g., machining or sanding.

While both of the embodiments illustrated in FIGS. 1, 2 and 3, are of illuminators prepared from filamentous bodies, as stated, other optically transmissive bodies may be used to form an illuminator in accordance with the invention. FIG. 4 illustrates an illuminator seen generally at 50 prepared from a rectangular shaped body of a material which, while transparent to light has a refractive index such that light will travel by substantially internal reflection therethrough. Examples of suitable materials include but are not limited to acrylics and styrenes, polymers and certain types of glass. This illuminator 50 is formed with a first region 52 of individual recesses 54. The recesses 54 are individually formed in a manner similar to the manner by which the recesses 27 are formed, that is, the recesses 54 are formed by machine cutting. Thus the recesses 54 will resemble in appearance the recesses 27.

In order to insure that light will travel in both directions through the optical fiber, or for that matter through any optically transmissive body, an illumination source should be positioned at both ends of the body, such as at the ends 16 and 18 of the illuminator 10 illustrated in FIG. 1. While a second light source such as an incandescent bulb may be positioned proximate both ends 16 and 18, it is preferable if a coating 30 of an illuminant material is applied to the end 18. This material will absorb and become illuminated by any light passing through the end 18. This coating is preferably white and may either be a white paint or a white polymeric material applied to the end 18. As the light passes through the end 18 this white coating is illuminated and functions as a secondary light source to redirect any light which would normally pass out of the end 18 back through the illuminator 10. An illuminator prepared in this manner will possess increased efficiency.

Referring to FIG. 5 while, as stated, the illuminator 10 of the invention may be used for any purpose which requires the illuminating of an area in accordance with a preferred embodiment, an illuminator, which for the purposes of this discussion will be the illuminator 10, is used to light defined transparent portions of a panel, an example of which is indicated generally at 32. This panel 32 may, for example, be an automotive dashboard panel formed with discrete areas 34 of transparency. These discrete areas of transparency 34 would typically be positioned at those locations of the panel to indicate the location of certain instrumentalities. For example, the transparent area 34 may indicate the location of the gas or oil gage or indicate the function of a particular actuator, e.g. the windshield wiper actuator. This transparent area 34 will also include an indicia masking such that as the light passes through the transparent area 34 this indicia will become pronounced. This will allow an individual facing the panel 32 to read the indicia.

Typically, the panel 32 which is substantially opaque will include one or more lineal arrays 36 of discrete areas of transparency 34. One illuminator 10 will be aligned with each of these lineal arrays 36 and be formed with a number of the defined region of recess 22 equal to and aligned with each of the discrete transparent areas 34. Thus, each of these discrete areas 34 will be illuminated by the light being emitted from the illuminator 10 at each of the defined region 22.

The efficiency of the illuminator 10 for either this embodiment or in general is increased by the proper positioning of a reflectors behind the illuminators 10, with two of reflectors being shown at 38 and 48. The reflectors 38 and 48 will direct the light towards the discrete transparent areas 34. These reflectors 38 and 48 may be conventional reflectors prepared from metalized surfaces to function as mirrors, or may be a strip of white material positioned behind the illuminator 10. The white material will reflect the light back towards the illuminator 10 and thus to the area of transparency of the panel 32.

Furthermore, when using more than one illuminator 10 behind a panel 32, the numerous illuminators 10 can be optically interconnected in series as illustrated in FIG. 3. By connecting the illuminators in this manner only a single light source 20 is needed to provide the desired illumination of all of the discrete transparent areas 34.

As illustrated, each of the adjacent illuminators 10 are serially connected by a mechanism generally indicated at 42. This mechanism 42 is coupled to the normally exposed ends 18 of each illuminator 10, such that the light which would normally pass through that end 18 is directed to the end 18 of the connected illuminator 10.

As illustrated, this mechanism 42 includes two prisms indicated at 44 and 46 which are mounted at the ends 18 of the respective illuminators 10. These prisms 44 and 46 are mounted such that their hypotenuse faces will be angling towards each other. Mounted between each of the prisms 44 and 46 is a conventional fiber optic 48. The light which would normally pass out the end 18 will enter the respective prisms 44 or 46 and be reflected off the hypotenuse face into the conventional fiber optic 48. This light will then enter the other of the prisms 44 or 46 to be reflected off the respective hypotenuse face in a similar manner into the other illuminator 10. This arrangement can be utilized for two or more illuminators 10 and thus eliminates the need for more than one light source 20.

The resulting device which includes the panel 32 and a plurality of illuminators 10. By either separately illuminating the individual illuminators 10 by numerous light sources 20 or by interconnecting the illuminators 10 in series by the mechanism 42 described or any equivalent mechanism, the illumination of the numerous transparent areas defined in a panel 32 is provided in an efficient manner.

Another application for the optical illuminators of the invention is in their substitution for conventional light bulbs in lighting fixtures. Specifically, numerous illuminators in accordance with the invention can replace conventional incandescent or fluorescent bulbs used in lighting panels, i.e., medical X-ray lighting panels. The advantage of utilizing the illuminators of the invention is a reduction in the cost of such illumination. This is because a single light source such as an incandescent bulb can be used to direct light through a multiplicity optical illuminators of the invention.

While the preferred embodiments have been described and illustrated, various modifications and substitutions may be made thereto without departing from the scope of the invention. Accordingly, it should be understood that the present invention has been described by way of illustration and not limitation.

What is claimed is:

1. An illuminator comprising:
   an elongated optically transmissive body characterized by substantially total internal reflection having formed therein one or more recesses, which recesses are defined by two opposing surfaces which angle inwardly from an exterior surface of said body toward each other for a distance substantially equivalent to from about two to about eighty percent of said body cross-sectional distance to define therebetween an included angle, which included angle is from about seventy to about one hundred ten degrees.

2. The illuminator of claim 1 wherein said body is an optical fiber.

3. The illuminator of claim 1 wherein said body is a substantially rectangularly shaped form.

4. The illuminator of claim 2 wherein said recesses are formed as one or more groups of contiguously positioned recesses.

5. The illuminator of claim 3 wherein said recesses are formed as one or more groups of contiguously positioned recesses.

6. The illuminator of claim 3 wherein said recesses are substantially triangularly shaped recesses.

7. The illuminator of claim 1 wherein said included angle is from about eighty-five to about ninety-five degrees.

8. The illuminator of claim 2 wherein said included angle is from about eighty-five to about ninety-five degrees.

9. The illuminator of claim 3 wherein said included angle is from about eighty-five to about ninety-five degrees.

10. The illuminator of claim 4 wherein said included angle is from about eighty-five to about ninety-five degrees.

11. The illuminator of claim 5 wherein said included angle is from about eighty-five to about ninety-five degrees.

12. The illuminator of claim 1 wherein said recesses are formed by two opposing surfaces which angle inwardly from said body exterior surface for a distance substantially equivalent to from about two to about twenty-six percent of said body cross-sectional distance.

13. The illuminator of claim 7 wherein said recesses are formed by two opposing surfaces which angle inwardly from said body exterior surface for a distance substantially equivalent to from about two to about twenty-six percent of said body cross-sectional distance.

14. The illuminator of claim 8 wherein said recesses are formed by two opposing surfaces which angle inwardly from said body exterior surface for a distance substantially equivalent to from about two to about twenty-six percent of said body cross-sectional distance.

15. The illuminator of claim 10 wherein said recesses are formed by two opposing surfaces which angle inwardly from said body exterior surface for a distance substantially equivalent to from about two to about twenty-six percent of said body cross-sectional distance.

16. The illuminator of claim 11 wherein said recesses are formed by two opposing surfaces which angle inwardly from said body exterior surface for a distance substantially equivalent to from about two to about twenty-six percent of said body cross-sectional distance.

17. The illuminator of claim 10 wherein said recesses are formed by two opposing surfaces which angle inwardly from said body exterior surface for a distance substantially equivalent to from about two to about sixteen percent of said body cross-sectional distance.

18. The illuminator of claim 16 wherein a first end of said filament is coated with a white or substantially white material.

19. The illuminator of claim 17 wherein first end of said filament is coated with a white or substantially white material.

20. The illuminator of claim 16 wherein at least a first surface of each of said recesses is roughened.

21. The illuminator of claim 17 wherein at least a first surface of each of said recesses is roughened.

22. A device comprising:
a panel which, while being substantially opaque, is formed with at least a first discrete area of transparency;
at least a first optically transmissive body characterized by substantially total internal reflection, which body is formed with at least a first defined region of a series of contiguously positioned recesses, each of said recess regions being aligned with one of said discrete areas of transparency and each of said recesses defined by two opposing surfaces which angle inwardly from an exterior surface of said body toward each other for a distance substantially equivalent to from about two to about twenty-six percent of said body cross-sectional distance to define therebetween an included angle, which included angle is from about seventy to about one hundred ten degrees.

23. The device of claim 22 wherein said body is an optical fiber.

24. The device of claim 23 wherein said included angle is from about eighty-five to about ninety-five degrees.

25. The device of claim 24 wherein said recesses are formed by two opposing surfaces which angle inwardly from said body exterior surface for a distance substantially equivalent to from about two to about sixteen percent of said body cross-sectional distance.

26. The device of claim 25 wherein said panel is formed to define a plurality of discrete areas of transparencies, with said discrete areas being aligned in one or more lineal arrays, and wherein said device includes a number of said filaments equal to and aligned with said number of lineal arrays.

27. The device of claim 26 wherein two or more of said filaments are serially connected by an optically transmissive means which transmits the light from one of said filaments to the other of said filaments.

28. The device of claim 27 wherein a first end of each of said filaments is coated with a white or substantially white material.

29. The device of claim 28 wherein a nonattached end of one of said serially connected filaments is coated with a white or substantially white material.

30. The device of claim 28 wherein a reflector is positioned at along a side of said filament, which side is opposite that side of said filament facing towards said panel.

31. The device of claim 29 wherein a reflector is positioned at along a side of said filament, which side is opposite that side of said filament facing towards said panel.

32. The device of claim 31 wherein said discrete locations include indicia which are illuminated by directing light through said discrete locations of transparency.

33. The device of claim 32 wherein said discrete locations include indicia which are illuminated by directing light through said discrete locations of transparency.

34. A device comprising two or more optically transmissive bodies characterized by substantially total internal reflection, which bodies are formed with at least a first defined region of a series of contiguously positioned recesses, wherein each of said recesses are defined by two opposing surfaces which angle inwardly from an exterior surface of said body toward each other for a distance substantially equivalent to from about two to about twenty-six percent of said body cross-sectional distance to define therebetween an included angle, which included angle is from about eighty-five to about ninety-five degrees.

35. The device of claim 34 wherein said body is an optical fiber and wherein said recesses are formed as one or more groups of contiguously positioned recesses.

36. The device of claim 35 wherein said recesses are formed by two opposing surfaces which angle inwardly from said body for a distance substantially equivalent to from about two to about twenty-six percent of said body cross-sectional distance.

* * * * *

UNITED STATES PATENT AND TRADEMARK OFFICE
CERTIFICATE OF CORRECTION

PATENT NO. : 4,765,701
DATED : August 23, 1988
INVENTOR(S) : Leonard W. Cheslak

It is certified that error appears in the above-identified patent and that said Letters Patent is hereby corrected as shown below:

Column 1, line 22, delete "numercus" and insert --numerous--

Column 1, line 18, delete "a" and insert --an--

Column 1, line 26, delete "in" and insert --is--

Column 1, line 25 between "than" and "bulb" insert --one--

Column 1, line 60 delete "be" and insert --been--

Column 2, line 17 delete "a" and insert --an--

Column 2, line 28 delete "optically" and insert --optical--

Column 2, line 45 between "accordance" and "an" insert --with--

Column 3, line 5 delete "a" and insert --an--

Column 3, line 57 delete "clouding" and insert --cladding--

Column 4, line 1 betweeb "such" and "to" insert --as--

Column 4, line 63 delete "surface" and insert --surfaces--

Column 5, line 15 delete "effect" and insert --affect--

Column 6, line 54 delete "gage" and insert --gauge--

Column 7, line 3, delete "a"

Column 7, line 42 delete "which"

Column 7, line 60 insert --of-- before "optical"

UNITED STATES PATENT AND TRADEMARK OFFICE
CERTIFICATE OF CORRECTION

PATENT NO. : 4,765,701

DATED : August 23, 1988

INVENTOR(S) : Leonard W. Cheslak

Page 2 of 2

It is certified that error appears in the above-identified patent and that said Letters Patent is hereby corrected as shown below:

Column 9, line 4, insert --a-- between "wherein" and "first"

Signed and Sealed this

Twenty-eighth Day of February, 1989

Attest:

DONALD J. QUIGG

Attesting Officer

Commissioner of Patents and Trademarks